United States Patent [19]

Izumori et al.

[11] Patent Number: 5,811,271
[45] Date of Patent: Sep. 22, 1998

[54] PROCESS FOR PRODUCING L-KETOHEXOSE

[75] Inventors: Ken Izumori, Kagawa; Keiji Tsusaki, Okayama, both of Japan

[73] Assignee: Kabushiki Kaisha Hayashibara Seibutsu Kagaku Kenkyujo, Okayama, Japan

[21] Appl. No.: 539,068

[22] Filed: Oct. 4, 1995

[30] Foreign Application Priority Data

Oct. 5, 1994 [JP] Japan ................................. 6-264406
Sep. 6, 1995 [JP] Japan ................................. 7-252038

[51] Int. Cl.⁶ ........................... C12P 19/02; C12P 19/24; C12P 19/00; C12N 9/58
[52] U.S. Cl. ........................... 435/105; 435/94; 435/233; 435/72
[58] Field of Search ............................ 435/105, 94, 233, 435/72

[56] References Cited

U.S. PATENT DOCUMENTS 5,411,880  5/1995  Izumori et al. ........................ 435/233

FOREIGN PATENT DOCUMENTS 0592202   4/1994   European Pat. Off. .
3-266996  11/1991  Japan .
5-308984  11/1993  Japan .
6-125776  10/1994  Japan .

OTHER PUBLICATIONS

Itoh et al, Biosci. Biotech. Biochem. 58(12):2168–2171 1994.

Buckingham et al, Dictionary of Organic Compunds, Eyre & Spottiswoode, vol. 3, p. 5097, 1936.

Abstract of Japanese Application No. 05–308,984, published 22 Nov. 1993.

*Primary Examiner*—Francisco C. Prats
*Attorney, Agent, or Firm*—Browdy and Neimark

[57] ABSTRACT

L-Ketohexoses such as L-fructose and L-tagatose are produced from L-psicose and L-sorbose as substrates by allowing D-ketohexose 3-epimerase to act on these substrates. The yield and the production cost of the produced L-fructose and L-tagatose are industrially acceptable. The enzyme is preparable from microorganisms, e.g. those of the genus Pseudomonas.

7 Claims, 1 Drawing Sheet

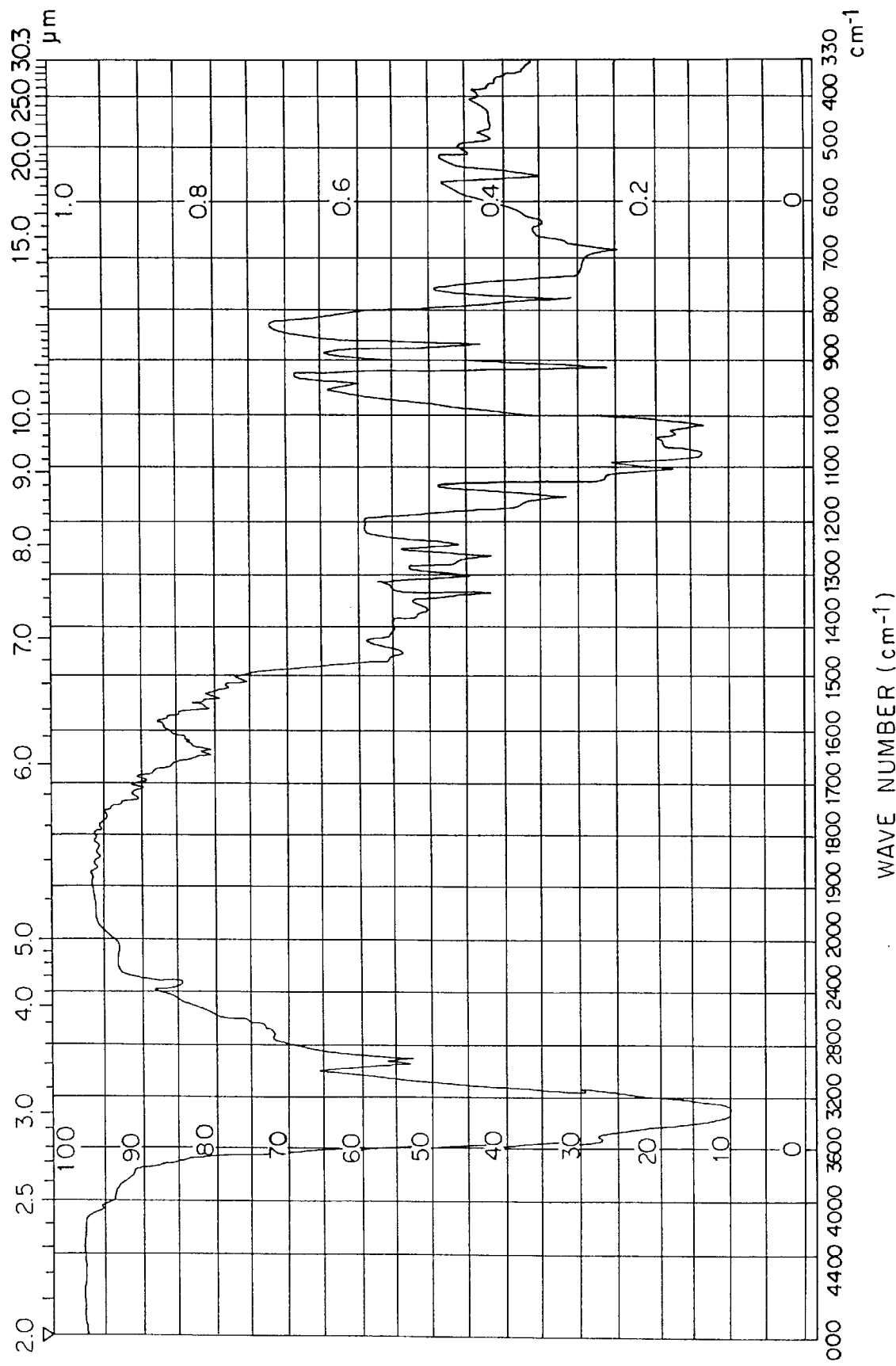

PROCESS FOR PRODUCING L-KETOHEXOSE

BACKGROUND OF THE INVENTION

1. Field of the Invention

The present invention relates to a preparation of L-ketohexose, more particularly, to a process for producing L-fructose and L-tagatose by allowing an L-fructose- and L-tagatose-forming enzyme to act on L-psicose and L-sorbose, respectively.

2. Description of the Prior Art

L-Fructose and L-tagatose are rare monosaccharides which belong to L-ketohexose and present in trace in the natural world. In principle, these monosaccharides can be produced by organic chemical methods: L-Fructose is produced by L-glucose and L-mannose under the coexistence of alkaline reagents such as sodium hydroxide, pyridine, etc. While, L-tagatose is produced by isomerizing L-galactose under the coexistence of alkaline reagents similarly as in the case of L-fructose. However, it is difficult to obtain L-glucose, L-mannose and L-tagatose as materials for L-fructose and L-tagatose, and no proper process for producing large amounts of L-fructose and L-tagatose is reported.

The present inventors disclosed in Japanese Patent Laid-Open No.308,984/93 a process for producing L-tagatose from galactitol using a bacterium of the genus Klebsiella. However, the process requires a relatively large amount of cells, preparation time, and complicated purification step. Therefore, it has not been actually practiced.

In recent years, biochemical industry has developed rapidly, and the development of new saccharides has been demanded in the field of carbohydrate chemistry. The mass-production of L-fructose and L-tagatose has not established. Therefore, these monosaccharides have not been used as industrial materials in the fields of food-, pharmaceutical-, chemical-industries, etc.

SUMMARY OF THE INVENTION

The present inventors screened biochemical methods which may enable the production of L-ketohexose such as L-fructose and L-tagatose in an industrial scale at a relatively low cost. As a result, the present inventors unexpectedly found that, as disclosed in Japanese Patent Laid-Open No.125,776/94, D-ketohexose 3-epimerase acts on L-ketohexoses, especially on L-psicose and L-sorbose to produce L-fructose from the L-psicose and L-tagatose from the L-sorbose, and have accomplished this invention.

BRIEF DESCRIPTION OF THE ACCOMPANYING DRAWING

The single drawing FIGURE is an infrared absorption spectrum of L-tagatose.

DETAILED DESCRIPTION OF THE INVENTION

D-Ketohexose 3-epimerases which are used in the present invention can be obtained by the cultivation of microorganisms capable of producing such D-ketohexose 3-epimerases.

Examples of such microorganisms are those of the genus Pseudomonas including *Pseudomonas cichorii* ST-24 (FERM BP-2736) and its mutants which are illustrated in Japanese Patent Laid-Open No.266,996/91.

D-Ketohexose 3-epimerases are usually prepared by cultivating for about 1–5 days microorganisms capable of producing such D-ketohexose 3-epimerases in liquid nutrient culture media containing carbon sources, nitrogen sources, inorganic salts, vitamins and the like, preferably, under aerobic conditions such as aeration-agitation conditions, and recovering the enzyme from cells and/or supernatant of the resultant cultures. Generally, the resultant cultures are used as crude D-ketohexose 3-epimerases. If necessary, the cultures can be partially purified by conventional methods such as filtration, centrifugation, salting out, dialysis, concentration and lyophilization, prior to use. In case that highly purified preparations are required, the cultures can be arbitrarily purified to the highest possible level by subjecting them to adsorption and desorption methods using ion-exchangers, gel filtration, isoelectrofocusing, electrophoresis, high-performance liquid chromatography (hereinafter abbreviated as "HPLC"), affinity chromatography and/or adsorption and desorption on monoclonal antibodies.

The D-ketohexose 3-epimerases or the microorganisms with the enzyme activity can be advantageously immobilized in usual manner for repeatedly using them in the conversion reaction of L-psicose and L-sorbose into L-fructose and tagatose, respectively, and in the continuous reaction. This type of conversion reaction is usually carried out under the following conditions: Substrate concentration, 1–60 w/v, preferably, about 5–50 w/v %; reaction temperature, a temperature in the range of 10°–70° C., preferably, about 30°–60° C.; reaction pH, a pH in the range of 5–10, preferably, in the range of about 7–10; and the amount of enzyme, at least one unit per gram of substrate, preferably, 10–5,000 units per gram of substrate, on a dry solid basis (d.s.b). The reaction time can be arbitrarily chosen, usually, from those in the range of 5–50 hours for a batchwise reaction with an economical view point.

The reaction mixtures thus obtained, which contain the newly formed L-fructose or L-tagatose and intact L-psicose or L-sorbose as starting materials, can be advantageously used intact as sweetener, moisture-imparting agent, crystallization-preventing agent and gloss-imparting agent. The reaction mixtures are generally prepared in usual manner into syrupy products by successively subjecting them to decoloration with activated charcoal, salting out and purification with ion exchangers in H- and OH-form, and concentration. The concentrates can be readily separated on column chromatographies using strongly-acidic cation exchangers in alkaline metal- or alkaline earth metal-form into a fraction rich in the newly formed L-fructose or L-tagatose, and a fraction rich in L-psicose or L-sorbose as a material, followed by purifying and concentrating the L-fructose- or the L-tagatose-rich fraction into a syrupy product and advantageously crystallizing the concentrate into a crystalline product, if necessary. The separated L-psicose- and L-sorbose-rich fractions can be recycled as starting material for the next conversion reaction.

The L-fructose and the L-tagatose thus obtained are advantageously usable as sweetener to impart an appropriate sweetness to orally administrable products such as foods, beverages, feeds, pet foods, dentifrices, cachous, sublingual agents and internal medicines, as well as to improve their taste qualities. These monosaccharides can be also advantageously used as carbon sources for fermentation, as well as a chemical reagent, material and intermediate for chemicals and pharmaceuticals.

The following experiment will explain the action of D-ketohexose 3-epimerase on L-ketohexose:

Experiment

D-Ketohexose 3-epimerase was studied for relative enzyme activity on various L-ketohexoses. A purified D-ketohexose 3-epimerase obtained by the method in Example 1 was allowed to act on four different types of L-ketohexoses as substrates, i.e. L-psicose, L-fructose, L-sorbose and L-tagatose, to determine the enzyme activity on them. The reaction conditions were as follows: To either substrate in 0.1 M solution (pH 7.5) was added 11 units/g substrate of the enzyme and reacted at 30° C. for 24 hours. As a control, D-tagatose was used as substrate and the relative enzyme activity was regarded as 100. The results were in Table 1.

TABLE 1

| Substrate | Relative enzyme activity |
| --- | --- |
| D-Tagatose | 100 |
| L-Psicose | about 20 |
| L-Fructose | about 5 |
| L-Sorbose | about 2 |
| L-Tagatose | about 0.5 |

As obvious from the results in Table 1, D-ketohexose 3-epimerase catalyzes the conversion reaction of L-ketohexose, especially, it converts L-psicose into L-fructose. The results also show that the conversion reaction is an equilibrium reaction, and the equilibrium point inclines to the L-fructose formation because L-psicose and L-fructose are formed in a weight ratio of about 3:7, d.s.b., meaning that it is suitable for L-fructose production. In addition, the results show that the conversion reaction of L-sorbose and L-tagatose is an equilibrium reaction.

The followings will show several preferred embodiments of the present invention:

Example 1

A nutrient culture medium consisting of 0.2 w/v % ammonium sulfate, 0.24 w/v % potassium phosphate monobasic, 0.56 w/v % potassium phosphate dibasic, 0.01 w/v % magnesium sulfate heptahydrate, 0.5 w/v % yeast extract, 1 w/v % D-glucose and deionized water was placed in a jar fermenter, sterilized at 120° C. for 20 minutes, and aseptically inoculated with 1 v/v % of a seed culture of *Pseudomonas cichorii* ST-24 (FERM BP-2736), followed by the cultivation at 30° C. for 40 hours under aeration-agitation conditions. The cells which had been recovered from 80 liters of the resultant culture were crushed by grinding in the presence of activated alumina followed by extracting the objective enzyme with 50 mM Tris-HCl buffer (pH 7.5).

The obtained crude enzyme solution was purified in the presence of manganese chloride by repeated fractional sedimentation using polyethylene glycol 6,000 (hereinafter abbreviated as "PEG"): Precipitates, which had formed in the crude enzyme solution at the PEG concentrations of 5–18 w/v % in the presence of 0.1 M manganese chloride, were collected and dissolved in a fresh preparation of the same buffer, and the step was repeated twice. The resultant solution was heated at 50° C. for 20 minutes, and the degenerated proteins were removed by centrifugation. The remaining proteins were purified by adsorbing on "DEAE-TOYOPEARL® 650M", a product of Tosoh Corporation, Tokyo, Japan, and the adsorbed substance was eluted with a potassium chloride solution. The purified product thus obtained was demineralized on an ultrafiltration using "TOYO ROSHI UK-10", a membrane filter commercialized by Toyo Roshi Kaisha, Ltd., Tokyo, Japan, concentrated and purified on a gel filtration using "SEPHADEX® G150", a product of Pharmacia LKB Biotechnology AB, Uppsala, Sweden. Fractions with an enzyme activity were concentrated and purified on an isoelectric focussing using "AMPHOLINE®", a product of Pharmacia LKB Biotechnology AB, Uppsala, Sweden.

The enzyme specimen thus obtained was assayed as follows: The reaction solution used in this assay consisted of 100 microliters of 50 mM Tris-HCl buffer (pH 7.5), 50 microliters 40 mM D-tagatose and 50 microliters of an enzyme solution. The enzymatic reaction was carried out at 30° C. for 60 minutes, and the formed D-sorbose was quantified on HPLC. One unit activity of the enzyme was defined as the amount of enzyme that epimerizes one micromol of D-tagatose into D-sorbose per minute.

The purification procedure was in Table 2.

TABLE 2

| Purification step | Protein (mg) | Enzyme activity ($\times 10^3$ unit) | Yield (%) | Purification (fold) |
| --- | --- | --- | --- | --- |
| Crude extract | 42,115 | 52,000 | 100.0 | 1 |
| PEG (first) | 8,378 | 50,580 | 97.3 | 4.4 |
| PEG (second) | 3,763 | 26,350 | 50.4 | 5.7 |
| Heat treatment | 3,207 | 27,800 | 53.6 | 7.0 |
| DEAE-TOYOPEARL ® | 415 | 17,220 | 33.1 | 33.6 |
| SEPHADEX ® G150 | 42.3 | 16,880 | 32.3 | 107.0 |
| Isoelectrofocusing | 3.0 | 1,078 | 2.1 | 291.0 |

As obvious from the results in Table 2, the purification procedure increased the specific activity of the enzyme by about 290 folds, in a yield of about 2%. Five w/v % aqueous L-psicose solution (pH 7.5) was mixed with 5,000 units/g L-psicose of the purified D-ketohexose 3-epimerase, and the mixture was enzymatically reacted at 40° C. for 30 hours. After completion of the reaction, the resultant reaction mixture was in usual manner decolored with activated charcoal, demineralized with "DIAION SK1B (H-form)" and "DIAION WA30 (OH-form)", products of Mitsubishi Chemical Industries Ltd., Tokyo, Japan, and concentrated in vacuo to obtain an about 60% transparent syrup containing L-fructose. The syrup was separated into L-fructose-and L-psicose-rich fractions on a column chromatography using "DOWEX 50W X4", a strongly-acidic cation exchanger of Dow Chemical Company, Midland, Mich., USA, purified, concentrated in usual manner, crystallized and separated to obtain a crystalline L-fructose in a yield of about 60% to the material, d.s.b.

The physicochemical properties of this product showed a good agreement with that of a standard L-fructose commercialized by Tokyo Chemical Industries, Ltd, Tokyo, Japan. The product is arbitrarily used as a sweetener, carbon source for fermentation, chemical regent, material, and intermediate in chemicals and pharmaceuticals. The enzyme reaction is a reversible reaction, and because of this, L-psicose is readily obtained by using L-fructose as a starting material.

Example 2

Ten w/v % aqueous L-psicose solution (pH 7.0) was mixed with 3,000 units/g L-psicose of a partially purified enzyme solution which had been obtained by subjecting a crude enzyme to the purification step in Example 1 up to the second PEG fractionation step, and the mixture was enzymatically reacted at 50° C. for 30 hours. After completion of the reaction, the reaction mixture was similarly as in Example 1 decolored, demineralized and concentrated in vacuo to obtain a transparent syrup containing about 70% L-psicose and L-fructose in a weight ratio of about 3:7 and in a yield of about 90%, d.s.b. The product is suitably used as a high-quality sweetener with a high-sweetening power, and advantageously used as a moisture-imparting agent, crystallization-preventing agent, gloss-imparting agent, and sweetening agent for foods and beverages.

Example 3

A partially purified enzyme solution, which had been obtained by subjecting a crude enzyme to the purification step in Example 1 up to the second PEG fractionation step, was fixed to "KITOPEARL BCW2503" of Fuji Spinning Co., Ltd., Tokyo, Japan. The partially purified enzyme was immobilized by adding it to the resin, followed by stirring at 30° C. for 2 hours. Finally, an about 80% activity of the enzyme was immobilized. Five w/v % aqueous L-psicose solution (pH 7.5) was mixed with 500 units/g L-psicose of the immobilized enzyme, and the mixture was enzymatically reacted at 45° C. for 40 hours. After completion of the reaction, the reaction mixture was similarly as in Example 1 decolored, demineralized and concentrated in vacuo to obtain a transparent syrup containing about 70% L-psicose and L-fructose in a weight ratio of about 3:7, d.s.b., in a yield of about 90%, d.s.b. The product is suitably used as a high-quality sweetener with a high sweetening-power, and advantageously used as a moisture-imparting agent, crystallization-preventing agent, gloss-imparting agent, and sweetening agent for foods and beverages.

Example 4

An immobilized D-ketohexose 3-epimerase, obtained by the method in Example 3, was added to 100 ml of 0.05 M phosphate buffer (pH 7.0) containing 4 w/v % L-sorbose, and reacted at 45° C. for 90 hours with shaking. The enzyme was separated by filtration.

The supernatant was in usual manner decolored with an activated charcoal, demineralized with "DIAION SK1B (H-form)" and "DIAION WA30 (OH-form)", products of Mitsubishi Chemical Industries Ltd., Tokyo Japan, and concentrated in vacuo to obtain an about 60% transparent syrup containing the intact material L-sorbose as an impurity. The syrup was purified on a column chromatography using "DOWEX 50W X4 (Ca-form)", a cation exchanger of Dow Chemical Company, Midland, Mich., USA, concentrated, crystallized and separated to obtain a crystalline L-tagatose. The yield of L-tagatose to L-sorbose was about 20%, d.s.b.

To identify the product obtained by this method, the present inventors studied the physicochemical property by experiments, compared the property with the authentic values, and compared with the data of a commercialized D-tagatose for a reagent, a product of SIGMA Chemical Company, ST. Louis, Mo., USA, as a standard substance.

(1) Melting point

Found for the present product : 134°–135° C. Authentic value of the commercialized D-tagatose: 133°–135° C.

Reference "Dictionary of Organic Compounds", 5th edition, Vol.3, page 5,097 (1982), Chapman and Hall, New York, USA.

(2) Measurement of specific rotation

Found for the product : $[\alpha]_D^{20}=+6.07$ (c=10%, $H_2O$)

Found for the commercialized D-tagatose: $[\alpha]_D^{20}=-5.78$ (c=10%, $H_2O$)

(3) Infrared absorption spectrum

The infrared absorption spectrum of this product measured by the KBr tablet method is in the single drawing figure. This spectrum well agreed with that of the authentic value.

(4) Analysis on high-performance liquid chromatography (HPLC)

The analysis of the product on HPLC using the following equipments and conditions of "880-PU" of JASCO Co., Tokyo, Japan; "GL-C611 COLUMN" of Hitachi, Ltd., Tokyo, Japan; eluent, $10^{-4}M$ sodium hydroxide; temperature, 60° C.; fluid speed, 1 ml/minute; and detector, "RID-6A" of Shimadzu Corporation, Tokyo, Japan, revealed that the elution time of the product was 22.2 minutes similar to that of D-tagatose, and the time differed from those of D-ketohexose such as D-psicose, D-fructose and D-sorbose as standard substances.

As obvious from the above result, the melting point of this product, infrared ray absorbed spectrum, and the analyzed value by HPLC had a good agreement with the authentic value of D-tagatose or the value of the standard substance. The measured specific rotation of the product almost agreed with that of D-tagatose, and their optical rotations (+, −) were opposite. This concludes that the product is L-tagatose.

The product according to the present invention can be used as a reagent, a rare saccharide, and advantageously used as a material and an intermediate in food-, pharmaceutical-, and chemical-industries.

As obvious from the above, this invention established a process using a biomedical method, which facilitates the production of L-fructose and L-tagatose that have been deemed very difficult to obtain. Especially, the finding of a process for producing L-fructose from L-psicose as a starting material by using D-ketohexose 3-epimerase has a great significance for the production of L-fructose, meaning that the process enables an industrial scale production of L-fructose because L-psicose as a starting material can be produced from D-tagatose and D-psicose by oxidation-reduction reaction. The finding of a process for producing L-tagatose from L-sorbose as a starting materials has a great advantage for the production because L-sorbose as a material is produced from sorbitol in an industrial scale and at a relatively low cost.

Thus the process according to the present invention is suitable as a process for industrially producing L-fructose and L-tagatose because it readily supplies these saccharides in an industrial scale and at a relatively low cost. Furthermore, the present invention opens the way of L-fructose and L-tagatose to be used in reagents as a rare saccharide and in food-, pharmaceutical-, and chemical-industries, the uses of which could not have been even imagined.

While there has been described what is at present considered to be the preferred embodiments of the invention, it will be understood the various modifications may be made therein, and it is intended to cover in the appended claims all such modifications as fall within the true spirit and scope of the invention.

We claim:

1. A process for producing L-ketohexose, which comprises allowing D-ketohexose 3-epimerase to act on a solution containing L-psicose or L- sorbose as a substrate to enzymatically produce L-fructose from said L-psicose or L-tagatose from said L-sorbose, and collecting the produced L-fructose or L-tagatose.

2. The process of claim 1, wherein said D-ketohexose 3-epimerase is derived from a microorganism of the genus Pseudomonas.

3. The process of claim 1, wherein said collecting step is one which recovers L-fructose or L-tagatose that has been separated and purified on a column chromatography using a strongly-acidic cation exchanger.

4. The process of claim 1, wherein the concentration for said substrate is in the range of 1–60 w/v %.

5. The process of claim 1, wherein said D-ketohexose 3-epimerase is allowed to act on said substrate at a temperature in the range of 10°–70° C. and a pH in the range of 5–10.

6. The process of claim 1, wherein said D-ketohexose 3-epimerase is used in an amount of 10–5,000 units per gram of substrate, on a dry solid basis.

7. A process for producing sweetener containing L-ketohexose, which comprises allowing D-ketohexose 3-epimerase to act on a solution containing L-psicose or L-sorbose to produce L-fructose from said L-psicose or L-tagatose from said L-sorbose, and collecting the resultant mixture.

* * * * *